United States Patent [19]

Messingschlager

[11] 4,449,974
[45] May 22, 1984

[54] BODY FLUID DRAINAGE TUBE

[76] Inventor: Walter Messingschlager, Rheinallee 1a, 4000 Dusseldorf 11, Fed. Rep. of Germany

[21] Appl. No.: 393,482

[22] Filed: Jun. 29, 1982

[30] Foreign Application Priority Data

Feb. 26, 1982 [DE] Fed. Rep. of Germany ....... 3206834

[51] Int. Cl.$^3$ ............................................ A61M 25/00
[52] U.S. Cl. ..................................... 604/175; 604/280
[58] Field of Search ............... 604/175, 174, 176, 179, 604/264, 93, 277, 244, 280; 3/1

[56] References Cited

U.S. PATENT DOCUMENTS

| | | | |
|---|---|---|---|
| 2,438,073 | 3/1948 | Saur | 604/277 |
| 3,807,409 | 4/1974 | Paperella, et al. | |
| 4,015,607 | 4/1977 | Wright | 604/264 |
| 4,217,664 | 8/1980 | Faso | 604/175 X |

FOREIGN PATENT DOCUMENTS

| | | |
|---|---|---|
| 3017065 | of 0000 | Fed. Rep. of Germany . |
| 3002298 | of 0000 | Fed. Rep. of Germany . |
| 125238 | of 0000 | German Democratic Rep. . |

*Primary Examiner*—Stephen C. Pellegrino
*Attorney, Agent, or Firm*—Sherman & Shalloway

[57] ABSTRACT

A drainage tube has a main body portion in which the distal or bottom end has an arch-like cross-section such that the distal end provides a protective shield to prevent blockage of the fluid inlet opening at the proximal or front end of the main body portion. An elongated slot-like drainage channel extends through the main body portion from the fluid inlet to a discharge opening at the distal end and assumes the same general convex-arch-like configuration as the main body portion. A flexible flange extends radially outwardly from the fluid inlet and a hollow stem member extends from the discharge opening in the distal end and provides an extension of the drainage channel. The stem also prevents the drainage tube from falling through the access in the body wall into the body cavity while the flange prevents the tube from being accidentally pulled out of the body cavity. A cut-out portion on the side of the stem opposite the flange member can be provided to form an access and guide for a probe to be inserted into the body cavity through the drainage channel.

7 Claims, 6 Drawing Figures

BODY FLUID DRAINAGE TUBE

BACKGROUND OF THE INVENTION

1. Field of the Invention

This invention relates to a drainage tube for draining body fluids from a body cavity. More particularly, this invention relates to a drainage tube adapted for insertion into a body cavity through an access thereto made by surgical procedure wherein the drainage tube is of the type including an elastic, flange-like projection at the inlet end of the tube so that the flange-like member may be inserted into the body cavity through the surgical access to prevent the tube from being inadvertently displaced from the body cavity.

2. Discussion of the Prior Art

U.S. Pat. No. 3,807,409 provides a medical ventilation tube which is useful for surgical ventilation and as a drain from the middle ear. The device is constructed of a flexible rubber material in a tubular shape having an inner and outer flange, the inner flange of which is substantially larger in diameter but thinner than the outer flange. The outer flange includes a special upstanding lip which assists in the grasping and removal of the tube. The construction and shape of this ventilation and drain tube limits its usefulness for insertion into the middle ear, i.e. ear drum, of the human ear and access to other body cavities is generally not possible.

German OS No. 30 02298 describes a drainage tube which also includes elastic flanges of variable sizes and shapes at both ends thereof. The shape of this drainage tube is designed to allow it to be inserted into an access leading to relatively narrow body cavities. The flanges, when viewed in a peripheral direction, may be subdivided into several parts in order to facilitate its insertion and removal. In addition, this design allows for the ingrowth of mucous membrane below the middle piece of the tube, for example from the nose into the maxillary sinus or vice versa.

In practice, these dual flange drainage tubes have several drawbacks. In the case of insertion and removal into body cavities of relatively difficult accessability, it is often not possible for the surgeon to control and coordinate hand/eye movement. Accordingly, in these cases, insertion and removal is accomplished essentially only with the help of the sense of touch or feel. However, the use of auxillary tools, such as a pair of pincers or forceps, to assist in handling the drainage tube is often not possible in view of the presence of the rear or outer flange.

Another disadvantage with these prior art drainage tubes is the fact that the opening of the drainage channel of the tube may be covered up by parts of the body wall located in the vicinity of the drainage tube. This could result in the disturbance or even complete stoppage of the drainage flow.

SUMMARY OF THE INVENTION

The present invention overcomes these drawbacks by providing a drainage tube that can be handled easily and at the same time insures a reliable maintenance of the drainage flow. Accordingly, the present invention provides a drainage tube for insertion into an access to a body cavity wherein the wall of the tube, defining the drainage channel, is in the shape of a convex arch extending from the inlet opening at the proximal end thereof to the outlet opening at the distal end thereof, an elastic flange member extending radially outwardly from the periphery of the proximal end of the drainage tube and a hollow stem member extending from the discharge opening at the distal end of the drainage tube in the same direction as the convex arch. When the drainage tube is inserted into the surgically created or naturally occurring access, the flange member will prevent the tube from being dislodged from the body cavity while body fluids may be drained through the drainage channel of the drainage tube and into the hollow stem member where it may be collected for discarding or for testing. By providing a stem member, rather than an outer flange, the insertion and removal of the drainage tube will be facilitated. In particular, the stem member may be grasped by pincers or forceps, for example, during insertion into the body cavity and again during removal of the drainage tube from the body cavity. Accordingly, there is no need to reach directly up to the access itself to insert or remove the tube.

Another advantage of the drainage tube of this invention is provided by the arched configuration such that the drainage tube extends from the access to the body cavity, outside the wall of the body in the shape of an arch which extends into the stem member. Accordingly, the drainage channel defined by the curved wall of the drainage tube is correspondingly arched. Therefore, the actual cross-section of the drainage channel including the discharge opening of the drainage tube is protected from being blocked by the adjacent areas of the body wall by the covering provided by the arched wall. This assures that the discharge opening will remain at least substantially open as long as the drainage tube is left in place.

In a preferred embodiment of the drainage tube, the hollow stem member includes an opening running along the length thereof on one side of the stem member. Preferably the opening extends from the distal end of the drainage channel and continues over substantially the entire length of the stem member, most preferably to the free end of the stem. Preferably, the opening in the stem results in a stem with a U-shaped cross-section or similarly, the stem comprises a substantially rectangular base with narrow upstanding and preferably smooth rounded walls.

The open hollow stem member has the advantage of further protecting the discharge opening from blockage and at the same time, serves as a guide, for example, for the introduction of a probe into the body cavity through the drainage tube. For this latter function, it is preferred that the opening of the stem is located on the outside of the stem, that is on the side of the stem farthest away from the inlet opening of the drainage tube, i.e. on that side which faces away from the wall of the body cavity in which the tube is inserted.

It is also preferred that the components of the drainage tube are formed as an integral unit, i.e. of one piece construction made from an elastic material, generally rubber or plastic of suitable quality for medical purposes. In order to combine the higher tearing strength and lower Shore hardness of rubber with the biocompatibility of plastic materials, it is preferred to use as the elastic material a rubber core provided with a thin plastic outer layer, at least on those portions of the rubber core which are expected to come into contact with the body cavity. A silicone layer is particularly suitable. This combination provides both a high tensile strength and good compatibility with human tissue.

The invention will now be described in greater detail in connection with the following description of a specific embodiment thereof and the accompanying drawings.

DETAILED DESCRIPTION OF THE INVENTION

The drainage tube, shown generally at 10, is produced as a unitary construction from any suitable biologically compatible flexible material, for example soft rubber with a silicone coating, or more generally, a soft pliable silicone rubber material. Tube 10 includes a main body portion 18 which is a generally tubular, bowl shaped wall, flange member 12 at the proximal end of the main body portion and extending radially outwardly from the periphery of drainage channel 11 which extends through the main body portion, and hollow stem member 14 extending from the distal end (bottom) of the main body portion in a direction which is generally parallel to the flange member and moving away from the drainage channel 11.

Figure 3:
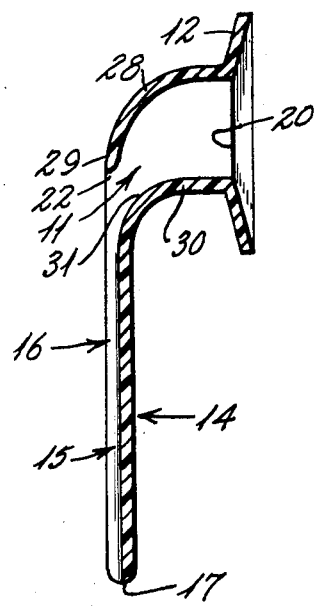
FIG. 3 is a side elevation sectional view in the direction of line 3—3 of FIG. 2.

Drainage channel 11 has an elongated slot-like cross-section which gradually converges in the direction of flow therethrough from the fluid inlet opening 20 at the front or proximal end of the main body portion towards the fluid outlet opening 22 at the rear or distal end of the main body portion. This cross-section of the drainage channel through the main body portion is provided by side walls 24 and 26 which are substantially straight over their entire lengths with a slight curvature towards the bottom (distal end) of the tubular wall main body portion, and curved upper and lower end walls 28 and 30, respectively. Each of curved end walls 28, 30 has a convex arched cross-section, as best seen in FIG. 3, at least in the distal end portion extending to the discharge opening 22, such that the bottom portion of main body portion 18, which is formed from the curved distal end portion 29 of end wall 28, together with the curved distal ends of side walls 24, 26 provide a protective shield for drainage channel 11. This protective shield assures that the drainage channel will remain open (unblocked) even if the drainage tube, including the outlet of the drainage channel, is covered or contacted by other body parts, clothing, bedding, etc. in the vicinity of the surgical access or other opening in the body wall leading to the body cavity being drained.

Hollow stem member 14 is shown extending from the bottom of the main body portion. In particular in the preferred embodiments illustrated in the figures, the stem member can be considered as a continuation of the curved distal end portion 31 of lower end wall 30 running away from the drainage channel in the same direction as the curved end portions 29 and 31, in a substantially straight path which is generally parallel to flange member 12.

Although the hollow stem member 14 can be closed around its entire circumference, similarly to the stem of a pipe, in the preferred embodiment illustrated in the figures, cut-out portion 15 is provided along the entire length of the stem member from the free end 17 of the stem extending to the peripheral edge 27 of end wall 28. Accordingly, the stem member has a generally U-shaped configuration with flat base 37 and slightly curved or rounded side walls 38,39.

Figure 5:
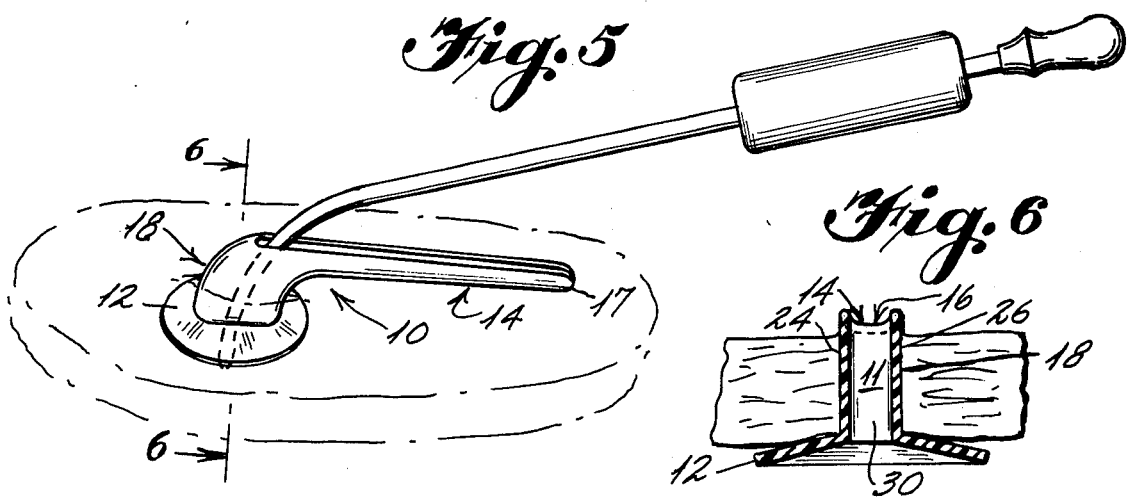
FIG. 5 is a perspective view of the discharge tube having a probe inserted through the drainage channel into the body cavity.
Figure 6:
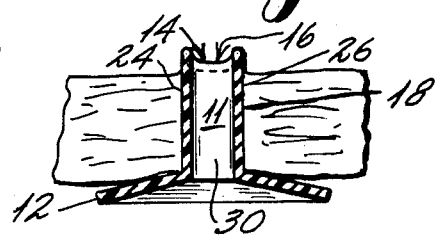
FIG. 6 is an end sectional view along line 6—6 of FIG. 5 showing the drainage tube inserted through a body wall into a body cavity.

The hollow stem provides an extension 16 of drainage channel 11 leading away from the body cavity being drained. By providing the cut-out portion 15, the resulting channel can also minimize the likelihood of totally blocking the flow path of the body fluids through combined drainage channel 11, 16. At the same time, as shown in FIG. 5, the channel in stem 14 functions as a guide for probe 50 or other device to be inserted into the body cavity through the drainage tube. For this purpose, and also to prevent the drained body fluids from contacting the body wall, the cut-out portion 15 is located on the back side of the stem member, i.e. on the side of the stem which is farthest away from the inlet opening and body wall. Since the wall of the stem member merges smoothly into the bottom or distal end of the main body portion there is no sharp edges or corners to impede or otherwise interfere with the flow of body fluids through the drainage channel and its extension provided by the hollow stem member.

Also, to facilitate the function of channel 16 as a guide for a probe or similar insert the peripheral edge 27 which defines one end of cut-out portion 15 is located within a zone defined by an imaginary projection perpendicular to the periphery of the inlet opening 20 so that the tip of the probe will have direct access to the body cavity through the opening between the peripheral edge 27 and peripheral edge 32 of end wall 30.

At the periphery of inlet opening 20, flange 12 extends radially outwardly, and is angled slightly, for example from about 5° to 30°, preferably 10° to 25°, with respect to a plane containing the inlet opening, to provide a funnel-like extension about the inlet opening. The angular or funnel-like configuration facilitates insertion and removal of the drainage tube into or from a body cavity. The angled flange also acts to guide and direct body fluids in the body cavity toward the inlet opening of the drainage channel.

Figure 4:
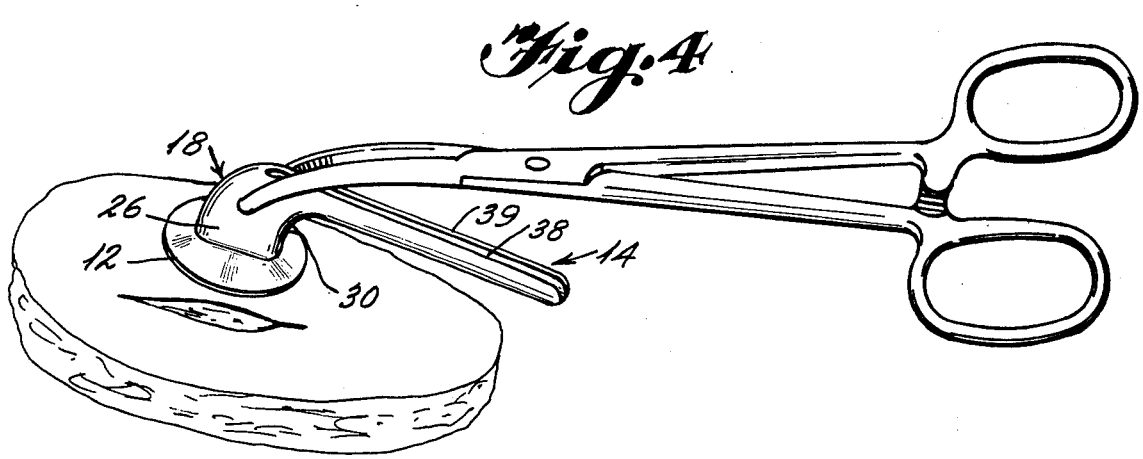
FIG. 4 is a perspective view of the drainage tube of FIG. 1 being handled for insertion and/or removal with a pair of forceps.

In practice, a surgical incision 1 is made in the body wall 2 to provide an access to the body cavity to be drained. The incision, as seen in FIGS. 4 and 5 should be slightly narrower than the outside width of the drainage channel, i.e. between flat side walls 24, 26 so that when the drainage channel is inserted there will be a tight fit between the drainage channel and the access. Because the drainage tube, including flange 12, is made from flexible material, it can be compressed, for example, by grasping with the forceps 40, to fit through the access during insertion. After the flange and drainage tube are fitted through the access to the body cavity the forceps are removed and the drainage tube expands to its original dimensions such that it will be held firmly in place by the body wall.

Flange 12 can abut against the inner surface of the body wall to prevent the tube from being accidentally withdrawn from the access while the stem member prevents the tube from accidentally slipping or being forced through the access into the body cavity. Since there is no flange at the distal end of the drainage tube, the tube can be readily grasped by forceps or other clamping device for insertion and removal of the tube into and from the body cavity.

FIG. 5 illustrates the insertion of a probe 50 into the body cavity using channel 16 as a guide for the tip of the probe. Since channel 16 extends to the distal end of the drainage tube, the tip of the probe has clear passage to the body cavity.

Figure 1:
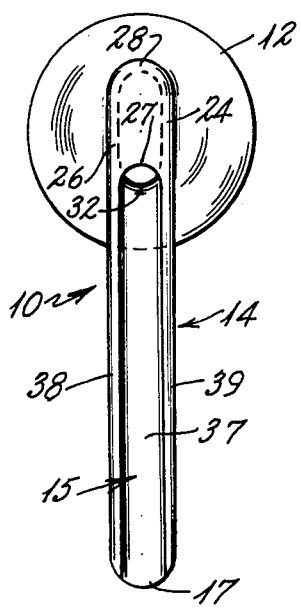
FIG. 1 is an elevation view from the rear of an embodiment of the drainage tube of this invention.
Figure 2:
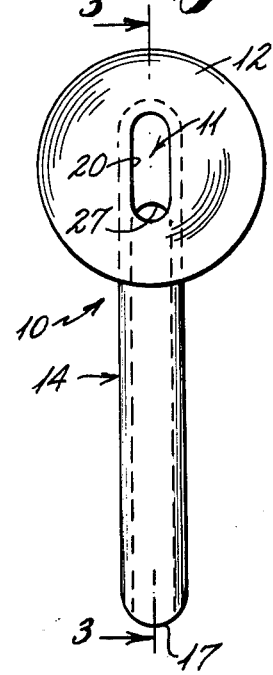
FIG. 2 is an elevation view from the front of the drainage tube of FIG. 1.

Although the drainage tube has been described in connection with a specific embodiment thereof, it is understood that the invention is not so limited. Various modifications can be readily envisioned by one of ordinary skill in the art and any such modifications which fall within the language of the appended claims are within the scope of this invention. For example, the cut-out portion 15 of stem member 14 can have a different configuration or can be entirely eliminated. Or only a perforation at or near the discharge opening of the drainage channel can be provided to permit a probe or other device to be inserted into the body cavity through the drainage channel. Side walls 24, 26 need not be flat but can also be curved to provide a more bowl-shaped drainage channel of elliptial or even circular cross-section. Stem member 14 can be shorter or longer than illustrated although it should extend at least beyond the edge of flange 12 (as viewed in FIGS. 1–3).

Still other modifications can be envisioned. Other biocompatible materials can be used. The flange member may be thinner or more flexible than the drainage channel or stem member, and the latter may be made from relatively inflexible or hard rubber if desired.

What is claimed is:

1. A drainage tube for insertion through an access in a body wall to a body cavity, said tube comprising
    a main body portion having a proximal front end portion and a distal bottom end portion with a drainage channel extending from a fluid inlet opening at the proximal front end to a fluid outlet opening at the distal bottom end, at least one wall segment of the distal end portion having a convex arch-like cross-section running from the proximal portion to the outlet opening, wherein the distal end provides a shield for protecting the drainage channel from being blocked,
    a flexible flange member extending radially outwardly from the fluid inlet opening, and
    a hollow stem member extending from the distal end of the main body portion as a continuation of, and in the same general direction as, the convex wall segment and away from the drainage channel, said hollow stem member extending in a substantially straight path which is substantially parallel to said flange member, and further wherein said hollow stem member has a cut-out portion extending along the entire length thereof on the side of the stem member which is furthest from the inlet opening, said cut-out stem member forming an open channel which is an extension of said drainage channel;
    whereby when said drainage tube is inserted into said access the flange member will prevent the tube from being dislodged from said body cavity and body fluids may be drained through the drainage channel and the hollow stem member.

2. The drainage tube of claim 1 wherein the main body portion comprises a pair of side walls which are substantially straight over their entire lengths with a slight curvature towards the distal end, a curved upper end wall and a curved lower end wall, said curved end walls connecting said side walls to form a tubular elongated bowl-shaped body, each of said curved end walls having a convex cross-section in at least the distal ends thereof, such that said drainage channel has an elongated slot-like cross-section.

3. The drainage tube of claim 2 wherein the radius of curvature of the convex portion of the upper end wall being greater than the radius of curvature of the convex portion of the lower end wall, whereby the elongated slot-like cross-section of the drainage channel converges in the direction of flow therethrough.

4. The drainage tube of claim 1 wherein the cut-out stem member has a U-shaped cross-section comprising a generally rectangular base and curved walls on either side of the base.

5. The drainage tube of claim 1 which is of unitary construction from a flexible biocompatible rubber.

6. The drainage tube of claim 5 wherein the biocompatible rubber is a silicone rubber.

7. A drainage tube for insertion through an access in a body wall to a body cavity, said tube comprising
    a main body portion having a proximal front end portion and a distal bottom end portion with a drainage channel extending from a fluid inlet opening at the proximal front end to a fluid outlet opening at the distal bottom end, at least one wall segment of the distal end portion having a convex arch-like cross-section running from the proximal portion to the outlet opening, wherein the distal end provides a shield for protecting the drainage channel from being blocked,
    a flexible flange member extending radially outwardly from the fluid inlet opening, and
    a hollow stem member extending from the distal end of the main body portion as a continuation of, and in the same general direction as, the convex wall segment and away from the drainage channel, said hollow stem member extending in a substantially straight path which is substantially parallel to said flange member and terminating in a converging substantially radiused free end;
    whereby when said drainage tube is inserted into said access the flange member will prevent the tube from being dislodged from said body cavity and body fluids may be drained through the drainage channel and the hollow stem member.

* * * * *